United States Patent [19]

Handin

[11] Patent Number: 5,321,127
[45] Date of Patent: Jun. 14, 1994

[54] ANTIPLATELET AND ANTITHROMBOTIC ACTIVITY OF PLATELET GLYCOPROTEIN IB RECEPTOR FRAGMENTS

[75] Inventor: Robert Handin, Needham, Mass.

[73] Assignee: Brigham and Women's Hospital, Boston, Mass.

[21] Appl. No.: 670,606

[22] Filed: Mar. 18, 1991

[51] Int. Cl.$^5$ .................. C07K 3/20; C07K 15/08; C07K 15/14; G01N 33/567
[52] U.S. Cl. .................. 530/383; 435/69.6; 436/501; 530/380; 530/413
[58] Field of Search ............... 530/395, 413, 383, 381, 530/359, 380; 514/822.8, 12, 21; 436/501; 435/69.1, 69.6

[56] References Cited

U.S. PATENT DOCUMENTS 5,055,556 10/1991 Stryer et al. .................. 436/501
5,200,510 4/1993 Kumar et al. .................. 530/383

FOREIGN PATENT DOCUMENTS 255206 2/1988 European Pat. Off. ............ 530/350
0295645 12/1988 European Pat. Off. .
10522 1/1984 Japan .................. 514/2

OTHER PUBLICATIONS

Sixma, J. J. et al., *J. Clin. Invest.* 74:736–744 (Sep. 1984).
Nurden, A. T. et al., *Nature* 255:720–722 (Jun. 1975).
Clemetson, K. J. et al., *J. Clin. Invest.* 70:304–311 (Aug. 1982).
Berndt, M. C. et al., *Eur. J. Biochem.* 151:637–649 (1985).
Wicki, A. N. et al., *Eur. J. Biochem.* 163:43–50 (1987).
Lopez, J. A. et al., *Proc. Natl. Acad. Sci. USA* 84:5615–5619 (Aug. 1987).
Lopez, J. A. et al., *Proc. Natl. Acad. Sci. USA* 85:2135–2139 (Apr. 1988).
Handa, M. et al., *J. Biol. Chem.* 261(27):12579–12585 (1986).
Vicente, V. et al., *J. Biol. Chem.* 263(34):18473–18479 (1988).
Michelson, A. D. et al., *Blood* 67(1):19–26 (1986).
Fox, J. E. B. et al., *J. Biol. Chem.* 263(10):4882–4890 (1988).
Coller, B. S. et al., *Blood* 61(1):99–110 (1983).
Miller, J. L. et al., *Brit. J. Haematology* 74:313–319 (1990).
Vicente, V. et al., *J. Biol. Chem.* 265(1): 274–280 (1990).
Bockenstedt, P. et al., *J. Clin. Invest.* 78:551–556 (Aug. 1986).
Katagiri, Y. et al., *Thromb. Haemst.* 63:122–126 (1989).
Bonthron, D. et al., *Nuc. Acids Res.* 14:7125–7127 (1986).
Mohri, H. et al., *J. Biol. Chem.* 263(34):17901–17904 (1988).
Mohri, H. et al., *J. Biol. Chem.* 264(29):17361–17367 (1989).
Pareti, F. I. et al., *J. Biol. Chem.* 262(28):13835–13841 (1987).
Titani, K. et al., *Proc. Natl. Acad. Sci. USA* 84:5610–5614 (Aug. 1987).
Wenger, R. H. et al., *Biochem. and Biophys. Res. Com* 156(1):389–395 (Oct. 1988).
Canfield, V. A. et al., *Biochem. and Biiophys. Res. Com.* 147(2):526–534 (Sep. 1987).
Coller, B. S., *Biorheology* 24:649–658 (1987).
Drouin, J. et al., *J. of Immunol. Methods* 110:217–223 (1988).

*Primary Examiner*—Jeffrey E. Russel
*Attorney, Agent, or Firm*—Sterne, Kessler, Goldstein & Fox

[57] ABSTRACT

A platelet glycoprotein Ib receptor fragment, having antiplatelet and antithrombotic activity, useful for blocking platelet adhesion. The invention may be used in the treatment of patients who are particularly prone to thrombosis and embolism. The invention may also be used to purify von Willebrands factor.

9 Claims, 8 Drawing Sheets

```
                                                Pst 1
                                                  |
5'-ATG CGC GCC CGG GGA TCC TCT AGA GTC GAC CTG CA G GAC AAT GCT GAA AAT——    SEQ. ID. NO. 1
   Arg Ala Arg Gly Ser Ser Arg Val Asp Leu Gln  Asp Asn Ala Glu Asn——
                                          221

Xba 1
                            |
——TCA TGG TCC ACT GCT TCT CTA G AG CTT ATC ATC ATC GAT GAT AAG CTG TCA
——Ser Trp Ser Thr Ala Ser Leu Gln Leu Ile Ile Ile Asp Asp Lys Leu Ser
                             318

AAC ATG AGA ATT AAA TCA ATC TAA-3'    SEQ. ID. NO. 2
Asn Met Arg Ile Lys Ser Ile STOP
```

FIG. 4 pT7-7   rGpIbα

ANTIPLATELET AND ANTITHROMBOTIC ACTIVITY OF PLATELET GLYCOPROTEIN IB RECEPTOR FRAGMENTS

STATEMENT AS TO RIGHTS TO INVENTIONS MADE UNDER FEDERALLY SPONSORED RESEARCH AND DEVELOPMENT

Part of the work leading to this invention utilized U.S. Government funds. The U.S. Government has certain rights in this invention.

FIELD OF THE INVENTION

The present invention relates generally to the fields of hematology and recombinant genetics. The invention specifically relates to recombinant platelet glycoprotein IB receptor fragments. In another aspect, it relates to the ability of these fragments to block platelet adhesion to the vessel wall. The invention also relates to the use of these receptor fragments for their antiplatelet antithrombotic activity.

DESCRIPTION OF THE PRIOR ART

Intravascular thrombosis and embolism are common clinical manifestations of many diseases. Unregulated activation of the hemostatic system has the potential to cause thrombosis and embolism, which can reduce blood flow to critical organs like the brain and myocardium. Certain patient groups have been identified that are particularly prone to thrombosis and embolism. These include patients (1) immobilized after surgery, (2) with chronic congestive heart failure, (3) with atherosclerotic vascular disease, (4) with malignancy, or (5) who are pregnant. The majority of "thrombosis prone" individuals have no identifiable hemostatic disorder, although there are certain groups of individuals having inherited or acquired "hypercoaguable" or "prethrombotic" conditions predisposing them to recurrent thrombosis. *Harrison's Principles of Internal Medicine*, 12th ed. McGraw Hill.

Effective primary hemostasis requires three critical events: platelet adhesion, granule release, and platelet aggregation. Within a few seconds of injury, platelets adhere to collagen fibrils in vascular subendothelium. This interaction is facilitated by von Willebrands factor, an adhesive glycoprotein which allows platelets to remain attached to the vessel wall despite the high shear forces generated within the vascular lumen. von Willebrand's factor accomplishes this task by forming a link between platelet receptor sites and subendothelial collagen fibrils.

As the primary hemostatic plug is being formed, plasma coagulation proteins are activated to initiate secondary hemostasis. There is little difference between hemostatic plugs, which are a physiological response to injury, and pathologic thrombi. Thrombosis is often described as coagulation which has occurred in the wrong place or at the wrong time. Hemostatic plugs or thrombi that form in veins where blood flow is slow are richly endowed with fibrin and trapped red blood cells and contain relatively few platelets. These thrombi often form in leg veins and can break off and embolize to the pulmonary circulation. Conversely, clots that form in arteries under conditions of high flow are predominantly composed of platelets and have little fibrin. These arterial thrombi may readily dislodge from the arterial wall and embolize to distant sites to cause temporary or permanent ischemia. This is particularly common in the cerebral and retinal circulation and may lead to transient neurologic dysfunction (transient ischemic attacks) including temporary monocular blindness (amaurosis fugax) or strokes. In addition, there is increasing evidence that most myocardial infarctions are due to thrombi which form within atherosclerotic coronary arteries. (The preceding discussion is taken primarily from *Harrison's Principles of Internal Medicine*, 12th ed., McGraw Hill.)

The binding of von Willebrand factor (vWF) to the platelet surface and to vascular subendothelium is an important step in primary hemostasis which permits platelets to remain adherent to vascular subendothelium under the high shear/flow conditions present within the microcirculation (Weiss, H. J., et al., *J. Lab. Clin. Med.* 92:750–764 (1978); Weiss, H. J., et al., *Am. J. Med.* 57:920–925 (1974)). vWF, which is an adhesive glycoprotein, links collagen and other constituents of subendothelium to receptor sites on platelet glycoproteins Ib/IX (GpIb/IX) and IIb/IIIa (Fujimoto, T., et al., *Nature* 297:154–156 (1982); Ruggeri, Z. M., et al., *J. Clin. Invest.* (1983)). vWF binds to two distinct receptors, which are located on glycoproteins Ib/IX and IIb/IIIa (Sixma, J. J., et al., *J. Clin. Invest.* 74:736–744 (1984); Fujimoto, T., et al., *Nature* 297:154–156 (1982)).

The GpIb/IX complex clearly plays a major role in hemostasis, as patients whose platelets are deficient in this glycoprotein complex have impaired platelet adhesion and a severe bleeding diathesis (Nurden, A. Y., et al., *Nature* 255:720–722 (1975); Clemetson, K. J., et al., *J. Clin. Invest.* 70:304–311 (1982)).

The glycoprotein Ib-IX receptor is made up of glycoproteins Ibα and β, which form a disulfide-linked heterodimer, and a third non-covalently linked subunit termed glycoprotein IX (Berndt, M. C., et al., *Biochem.* 137:637–649 (1985); Wicki, A. N., et al., *Eur. J. Biochem.* 163:43–50 (1987)).

The molecular cloning of the GpIbα (Lopez, J. A., et al., *Proc. Natl. Acad. Sci. U.S.A.* 84:5614–5619 (1987)), GpIbβ (Lopez, J. A., et al., *Proc. Natl. Acad. Sci. U.S.A.* 85:2135–2139 (1988)) and GpIX (Hickey, M. J., et al., *Proc. Natl. Acad. Sci. U.S.A.* 86:6773–6777 (1989)) cDNAs has provided information on the primary structure of the receptor subunit polypeptides which can be used to analyze the relationship between receptor structure and function. The GpIbα polypeptide is of particular interest as it contains the receptor's vWF binding site (Handa, M., et al., *J. Biol. Chem.* 261:12579–12585 (1986); Vincente, V., et al., *J. Biol. Chem.* 263:18473–18479 (1988)). Moreover, there is evidence that soluble fragments of GpIbα, produced by the incubation of platelets with proteolytic enzymes, can inhibit vWF binding to intact platelets. Glycocalicin (GC), which contains the majority of the extracellular portion of the GpIbα chain, is the most well characterized receptor fragment (Okumura, T., et al., *J. Biol. Chem.* 251:5944–5949 (1976)). It has been previously shown that purified GC can inhibit ristocetin-dependent binding of vWF to platelets (Michelson, A. D., et al., *Blood* 67:19–26 (1986)). It is cleaved from the surface of intact platelets by various maneuvers which activate platelet calpain, an endogenous calcium dependent protease (Fox, J. E., et al., *J. Biol. Chem.* 263:4882–4890 (1988)). Further digestion of glycocalicin with trypsin separates a small carboxy terminal carbohydrate-rich macroglycopeptide from an amino terminal 45 kDa fragment which contains the vWF binding site (Okumura, T., et al., *J. Biol. Chem.* 251:5950-5955 (1976)).

SUMMARY OF THE INVENTION

In order to obtain human platelet glycoprotein Ib receptor fragments which block platelet adhesion, the present inventor therefore attempted, and herein describes, a fragment derived from the glycoprotein Ibα polypeptide chain containing the vWF binding site. Further cDNA encoding the glycoprotein Ibα polypeptide has been cloned and expressed in *E. coli*.

The recombinant polypeptide (rGIbαQ$_{221}$-L$_{318}$) has been expressed with the prokaryotic vector pT7-7 and purified from inclusion bodies by denaturation, reduction, renaturation, and affinity chromatography on monoclonal anti-GpIbα columns. Purified soluble rGpIbαQ$_{221}$-L$_{318}$ inhibited ristocetin-dependent binding of [$^{125}$I]-vWF to fixed washed human platelets and the spontaneous binding of [$^{125}$I]-vWF to immobilized fibrillar Types I and III collagen.

The following Examples demonstrate that the vWF binding site on GpIbα lies between Q221 and L318, and that the binding of rGpIbαQ$_{221}$-L$_{318}$ to vWF inhibits binding of vWF to platelet bound GpIb/IX and to collagen. The recombinant receptor fragment presented by the inventor, rGpIbαQ$_{221}$-L$_{318}$, contains the entire sequence needed for recognition and binding to vWF. This recombinant polypeptide produced by transfection of GpIbα cDNA into heterologous cells can block vWF binding to platelets with high affinity. The receptor fragments are also unique in that they have the ability to block not only vWF (von Willebrands Factor) binding to GpIb but vWF interactions with collagen as well.

In Example I, (infra) employing deletion mutagenesis and transient expression of full GpIbα cDNA in COS cells, the vWF interaction site was mapped on the GpIb/IX complex to a 97 amino acid hydrophilic segment of the GpIbα chain (Petersen, E., et al., *J. Biol. Chem.* (submitted)). Although Example I localized a region of the GpIbα polypeptide which inhibits vWF binding to platelets, participation in the GpIb-vWF interaction by other segments of the GpIb/IX complex could not be excluded. In Example II, (infra) the expression, purification, and analysis of the properties of this 97 amino acid fragment of GpIbα document that this recombinant polypeptide retains biologic activity in several in vitro assays. The activity of these receptor fragments is unique in that it is the first instance of a platelet receptor protein having the ability to block platelet adhesion rather than platelet aggregation.

It is an object of the present invention, then, to provide for a method of treatment for individuals prone to thrombosis and embolism. The present invention thus provides an important advance in the therapy of thrombosis and embolism.

The work presented here demonstrates that recombinant platelet glycoprotein Ib receptor fragments may be used to block platelet adhesion without blocking platelet aggregation. The production of recombinant platelet glycoprotein Ib receptor fragments makes possible new treatments for intervascular thrombosis and embolism.

Thus in one embodiment, there is provided according to the invention recombinant, functionally active human platelet glycoprotein Ib receptor fragment, or a functional or chemical derivative thereof.

In yet another embodiment is provided a method for blocking platelet adhesion. Yet another embodiment of this invention comprises fragments that are capable of blocking vWF binding to collagen.

In another embodiment is provided the human platelet glycoprotein Ib receptor fragment which is produced by eukaryotic cells. Yet another embodiment of the invention comprises the plasmid pT7-7-GpIbα. There is also provided according to this invention, methods of producing human platelet glycoprotein Ib receptor fragments, comprising culturing the transformed cell under conditions allowing expression of the receptor fragment, and recovering said platelet glycoprotein Ib receptor fragment.

In yet another embodiment, the present invention provides for an antibody against the platelet glycoprotein Ib receptor fragment of the invention.

Further, a method of detecting human vWF in a sample is provided according to the present invention, comprising contacting said sample with the human platelet glycoprotein Ib receptor fragment, wherein said fragment is detectably labeled so as to form a complex between human vWF in said sample and said detectably labeled fragment, and detecting said complexed or uncomplexed detectably labeled fragment.

Moreover, a method of purifying von Willebrands factor from a sample comprising contacting said sample containing vWF with either human glycoprotein Ib receptor fragment or an anti-idiotypic antibody to said fragment, so as to form a complex between said human vWF in said sample and said fragment or antibody, and removing the vWF from said fragment or antibody so as to obtain purified human vWF.

An additional embodiment of the current invention comprises a pharmaceutical preparation comprising the recombinant platelet glycoprotein Ib receptor fragment. In another embodiment, there is provided a method of treating intervascular thrombosis and embolism with the pharmaceutical preparation of the invention, or a functional or chemical derivative thereof.

These and other non-limiting embodiments of the present invention will be apparent to those of skill from the following detailed description of the invention.

Platelets were separated from unbound ligand by centrifugation through a 5% sucrose cushion and platelet-associated radioactivity measured in a gamma spectrometer. Non-specific binding was determined with a 35 fold excess of non-radioactive vWF and is subtracted from each point. Non-specific binding never exceeded 20% of total binding. The data is plotted as the amount $[^{125}I]$-vWF bound compared to the amount bound with no competing ligand. The data plotted represents the mean values for three separate experiments each carried out in duplicate. The concentration of rGpIbα polypeptide was determined by ELISA using a polyclonal rabbit antihuman antibody (Michelson, A. D., et al., *Blood* 67:19–26 (1986)).

Figure 2:
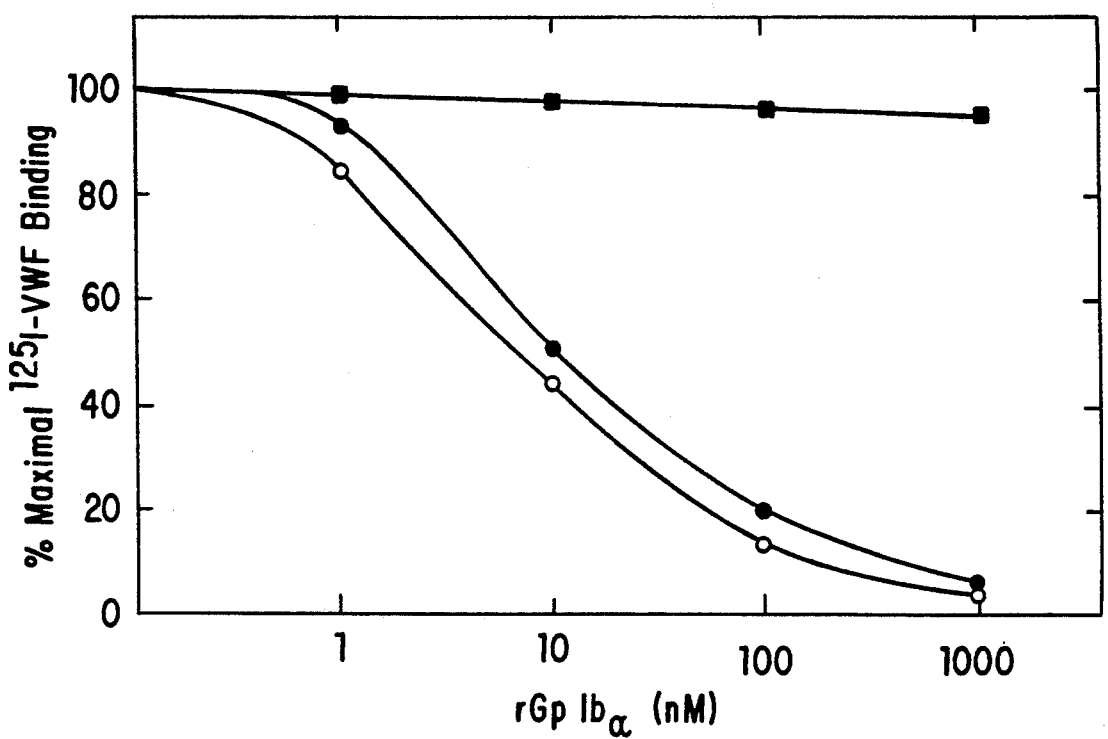
FIG. 2—Inhibition of [$^{125}$I]-vWF binding to platelets by glycocalicin and rGpIbα polypeptides. Conditioned medium from COS 7 cells that had been transfected with either pCDN8-GpIbαXbal or pCDM8-GpIbαPstI was harvested, lyophilized and resuspended to concentrate the rGpIbα polypeptides 10 to 50 fold. The binding of [$^{125}$I]-vWF was analyzed in $1 \times 10^8$/ml suspensions of fixed washed platelets containing 5 μg/A [$^{125}$I]-vWF and increasing concentrations of either glycocalicin (open circles) rGpIbαL$_{318}$ (closed circles) or rGpIbαL$_{220}$ (closed boxes). Binding was initiated by the addition of 1 mg/ml final concentration of ristocetin.
Figure 3:
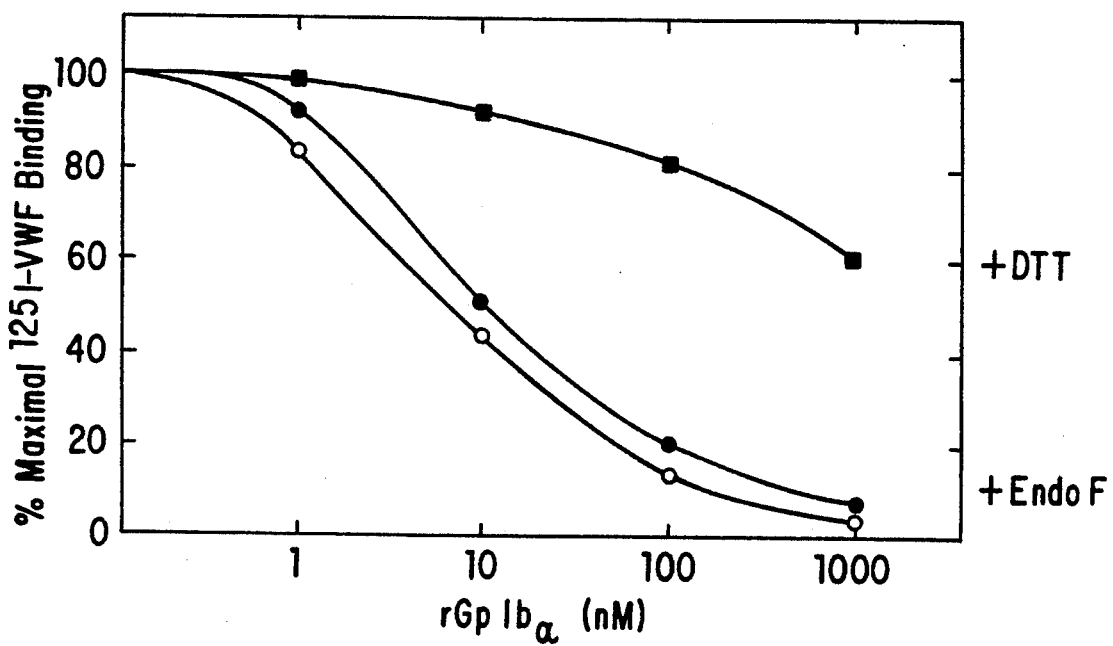

FIG. 3—Effect of disulfide reduction and N-deglycosylation on the biologic activity of rGpIbαL$_{318}$. Conditioned medium from COS 7 cells transfected with pCDM8-GpIbαXbaI was harvested and aliquots either incubated with 100 dithiothreitol (DTT) followed by 1 mN iodoacetamide or endoglycosidase F (ENDO F). The conditioned medium was then dialyzed against 20 mM Tris-HCl, pH 8.0 and concentrated 10 to 50 fold by lyophilization and then dialyzed into PBS. Untreated conditioned medium was treated identically. The binding of $[^{125}I]$-vWF to fixed washed platelets induced by ristocetin is depicted. Increasing concentrations of untreated (open circles), endoglycosidase F treated (closed circles) and reduced and alkylated (closed boxes) medium were added to suspensions containing $3 \times 10^8$ fixed washed platelets, 5 μg/ml $[^{125}I]$-vWF. Aggregation was initiated with 1 mg/ml ristocetin and the samples processed as described in FIG. 2 and Example I (infra). The concentration of rGpIbα polypeptide was determined by ELISA using a polyclonal rabbit antihuman antibody (Michelson, A. D., et al., *Blood* 67:19–26 (1986)).

FIG. 4—Construction of the GpIbα expression plasmid in pT7-7. The nucleotide sequence surrounding the cloning site is shown above with the translated amino acid sequence shown below. The location of the Pst 1 and Xba 1 restriction sites used to ligate the GpIbα cDNA fragment are identified and the nucleotides and amino acids contributed by GpIbα cDNA are marked in bold letters while the vector sequences are in regular type. As noted in addition to GpIbα sequence from glutamine 221 through leucine 318, the vector sequence contributes 10 additional amino terminal and 16 additional carboxy terminal amino acids to the recombinant protein.

Figure 5A:
Figure 5B:
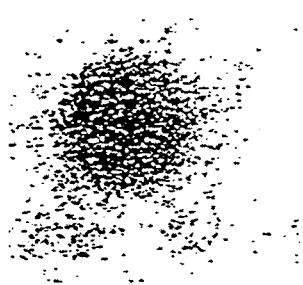

FIGS. 5A and 5B—Binding of $[^{125}I]$-vWF to bacterial extract containing rGpIbαQ$_{221}$-L$_{318}$. Dilutions (1:50) of pT77GpIbα and non-recombinant pT7-7 bacterial lysate prepared by incubation with lysozyme, freeze-thaw lysis and sonication, as described in Example II (supra), were adsorbed onto Immobilon membranes in a dot blotting apparatus. The bacteria were washed with TBS-T buffer and then incubated in 5% skim milk for several hours followed by the addition of 5 μg/ml final concentration of $[^{125}I]$-vWF and washed again with several changes of TBS-T. The bacteria had been cultured overnight at 30° C. and then incubated at 42° C. for 4 hours to derepress the T7 RNA polymerase promoter and induce recombinant protein synthesis.

Figure 6:
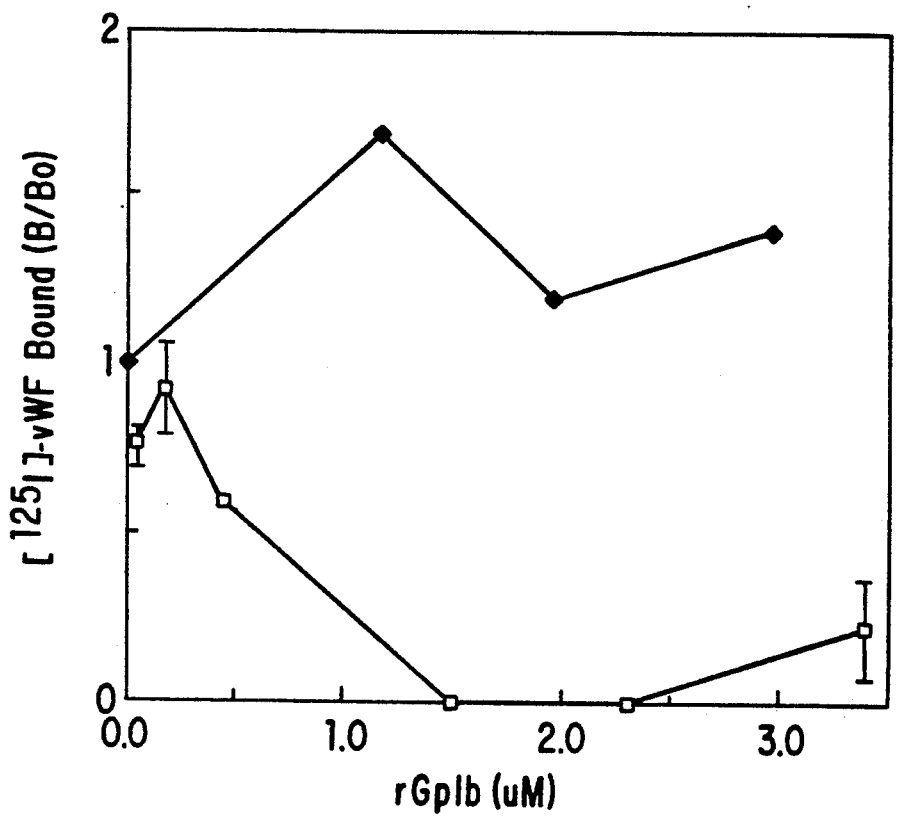

FIG. 6—Inhibition of ristocetin-dependent binding of $[^{125}I]$-vWF to paraformaldehyde-fixed washed platelets by native and reduced-alkylated rGpIbαQ$_{221}$-L$_{318}$. A final concentration of $1 \times 10^8$ platelets/ml was incubated in TBS buffer containing 5 μg/ml $[^{125}I]$-vWF and increasing concentrations of rGpIbαQ$_{221}$-L$_{318}$. Binding was initiated with 1 mg/ml ristocetin and platelet bound ligand separated after 30 minutes incubation by centrifugation at 12,000 g over a cushion of 500 μl of 50% sucrose. Platelet-associated radioactivity was determined in a gamma spectrometer. In each case nonspecific binding was measured in parallel tubes containing a 35 fold molar excess of non-radioactive vWF and was subtracted from each point. The results are plotted as B/B$_o$—the ratio of $\{^{125}I\}$-vWF bound to that bound with no competing ligand. The open box represents native purified rGpIbαQ$_{221}$-L$_{318}$ and the closed diamond inhibition by reduced alkylated polypeptide. The experiments depicted represent the $\bar{x} \pm$ S.E.M. for six separate studies each carried out in duplicate.

Figure 7:
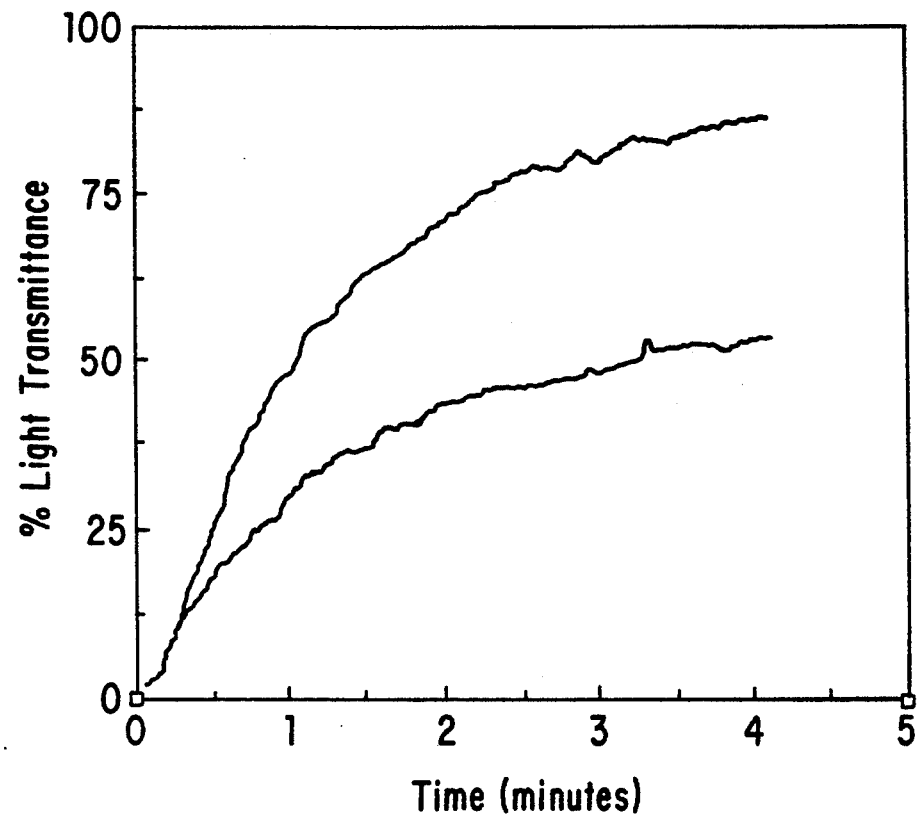

FIG. 7—Inhibition of ristocetin-dependent agglutination of paraformaldehyde-fixed washed platelets by rGpIbαQ$_{221}$-L$_{318}$. Aggregation of a $3 \times 10^8$/ml platelet suspension containing 10 μg/ml affinity purified vWF and increasing concentrations of rGpIbαQ$_{221}$-L$_{318}$ was initiated by the addition of a final concentration of 1.5 mg/ml ristocetin. Platelets were stirred continuously at 1,200 rpm at 37° C. in siliconized cuvettes and the change in light transmission recorded. The upper tracing is of aggregation with no added recombinant polypeptide and the lower tracing shows aggregation in the presence of 500 nM final concentration rGpIbαQ$_{221}$-L$_{318}$.

Figure 8:
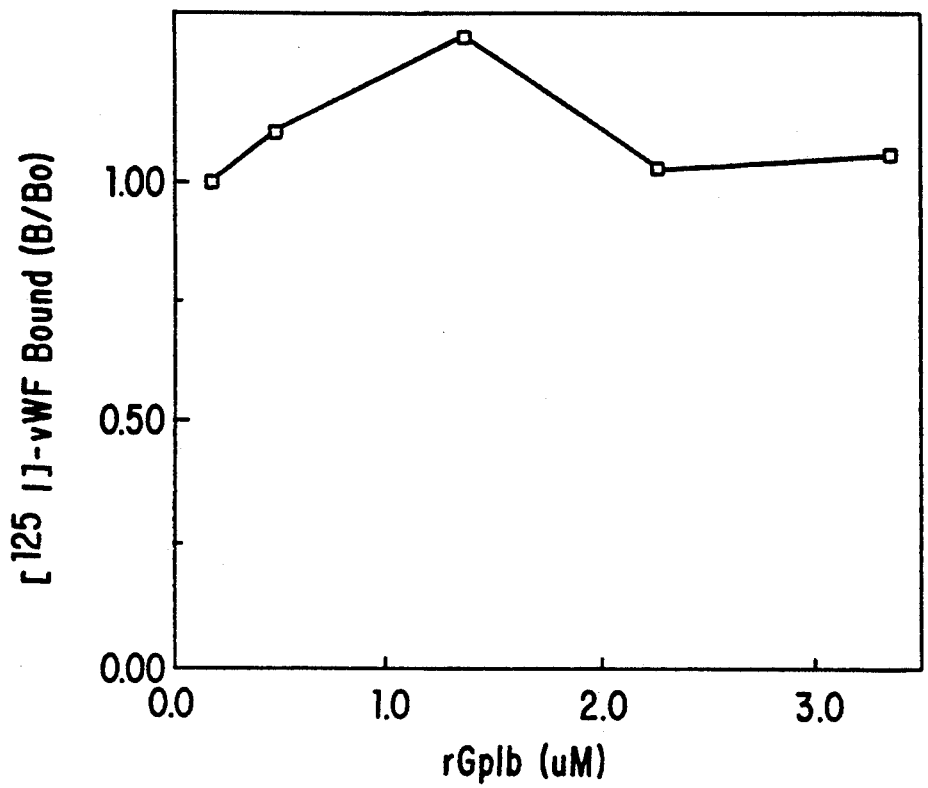

FIG. 8—Effect of rGpIbαQ$_{221}$-L$_{318}$ on ADP induced binding of $[^{125}I]$-vWF to freshly washed human platelets. The binding of $[^{125}I]$-vWF to a suspension of fresh platelets in the presence of increasing concentrations of rGpIbαQ$_{221}$-L$_{318}$ was carried as described in the text. Aggregation was initiated with a final concentration of 10 μM ADP. Platelets were washed free of all plasma proteins including vWF by gel filtration over Sepharose 2B followed by centrifugation on a BSA gradient. The data shown represents a single experiment.

Figure 9:
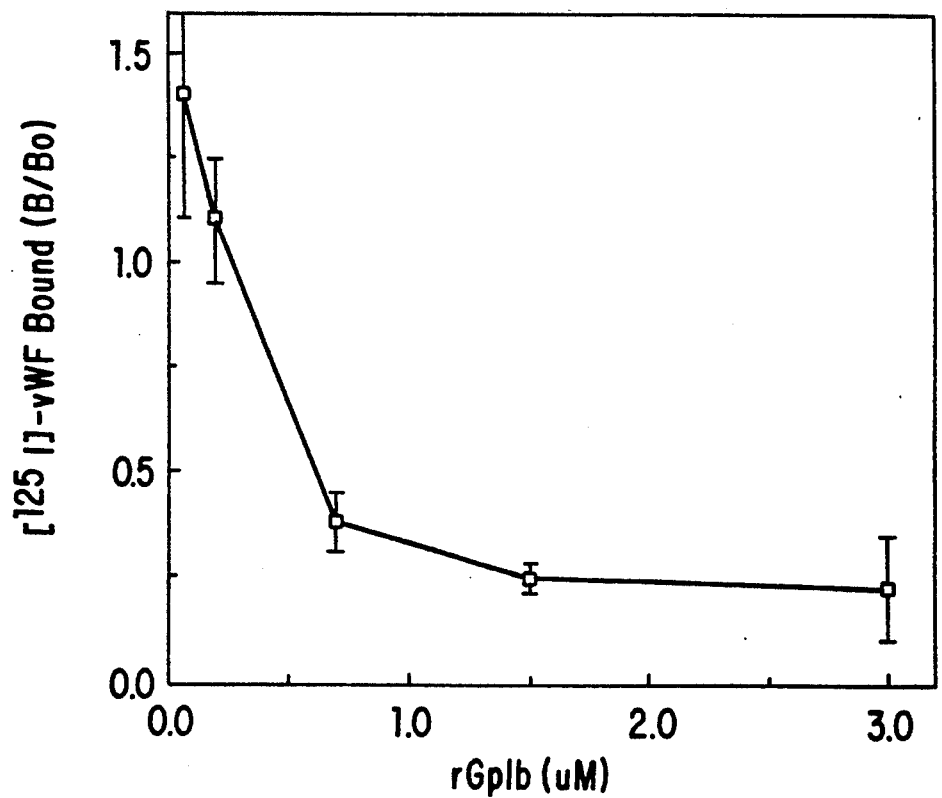

FIG. 9—Inhibition of $[^{125}I]$-vWF binding to collagen coated microtiter wells by rGpIbαQ$_{221}$-L$_{318}$. Microtiter wells were coated with Type I and III collagen by addition of acid soluble collagen in 20 mM citrate buffer, pH 6.1 and then raising the pH with TBS. Non-specific binding sites were then blocked by incubation with 1 mg/ml BSA for 60 minutes. Ten μg/ml $[^{125}I]$-vWF was then added to each well along with increasing concentrations of rGpIbαQ$_{221}$-L$_{318}$. After 30 minutes at 25° C., wells were washed three times with TBS-10 mg/ml BSA and radioactivity remaining in each well assessed by gamma spectrometry. Non-specific binding, as defined by a 35 fold excess of non-radioactive vWF, never exceeded 20% of total binding. The data is plotted as B/B$_o$—the ratio of $[^{125}I]$-vWF bound to that bound with no added competing ligand. The $\bar{x} \pm$ S.E.M. for six experiments each done in duplicate is plotted.

DESCRIPTION OF PREFERRED EMBODIMENTS

In the following description, reference will be made to various methodologies known to those of skill in the art of molecular biology and immunology. Publications and other materials setting forth such known methodologies to which reference is made are incorporated herein by reference in their entireties as though set forth in full.

Standard reference works setting forth the general principles of recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); and Maniatis, T., et al., *Molecular Cloning: A Laboratory Manual.* 2nd Ed. Cold Spring Harbor Laboratory, publisher, Cold Spring Harbor, N.Y. (1989).

DEFINITIONS

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise the entire genome of an organism. Such a cDNA library may be prepared by methods known to those of skill, and described, for example, in Maniatis et al., *Molecular Cloning: A Laboratory Manual*, supra. Generally, RNA is first isolated from the cells of an organism from whose genome it is desired to clone a particular gene. Preferred for the purposes of the present invention are mammalian, and particularly human, lymphocytic cell lines. A presently preferred vector for this purpose is the pT7-7 strain.

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible. Thus, by "DNA expression vector" is meant any autonomous element capable of replicating in a host independently of the host's chromosome, after additional sequences of DNA have been incorporated into the autonomous element's genome. Such DNA expression vectors include bacterial plasmids and phages.

By "substantially pure" is meant any antigen of the present invention, or any gene encoding any such antigen, which is essentially free of other antigens or genes, respectively, or of other contaminants with which it might normally be found in nature, and as such exists in a form not found in nature. By "functional derivative" is meant the "fragments," "variants," "analogues," or "chemical derivatives" of a molecule. A "fragment" of a molecule, such as any of the cDNA sequences of the present invention, is meant to refer to any nucleotide subset of the molecule. A "variant" of such molecule is meant to refer to a naturally occurring molecule substantially similar to either the entire molecule, or a fragment thereof. An "analog" of a molecule is meant to refer to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences*, 16th ed., Mack Publishing Co., Easton, Pa. (1980).

Similarly, a "functional derivative" of a gene of the adhesion blocking GpIbα platelet receptor fragment of the present invention is meant to include "fragments," "variants," or "analogues" of the gene, which may be "substantially similar" in nucleotide sequence, and which encode a molecule possessing similar activity to the rGpIbα$Q_{221}$-$L_{318}$ peptide.

Thus, as used herein, adhesion blocking GpIbα platelet receptor fragment is also meant to include any functional derivative, fragments, variants, analogues, chemical derivatives which may be substantially similar to the peptide rGpIbα$Q_{221}$-$L_{318}$ and which possess similar activity.

A DNA sequence encoding the adhesion blocking GpIbα platelet receptor fragment of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a platelet glycoprotein Ib receptor fragment encoding sequence) are said to be operably linked if the nature of the linkage between the two DNA sequences does not (1) result in the introduction of a frame-shift mutation, (2) interfere with the ability of the promoter region sequence to direct the transcription of the platelet glycoprotein Ib receptor fragment gene sequence, or (3) interfere with the ability of the platelet glycoprotein Ib receptor fragment gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

The present invention encompasses the expression of the adhesion blocking GpIbα platelet receptor fragment protein (or a functional derivative thereof) in either prokaryotic or eukaryotic cells, although prokaryotic expression is preferred. Examples of suitable prokaryotic and eukaryotic host cells include, but are not limited to, *E. coli*, COS cells, CHO cells, Sf9 cells and Sf9 cells.

Antibodies according to the present invention may be prepared by any of a variety of methods. For example, cells expressing the adhesion blocking GpIbα platelet receptor fragment protein, or a functional derivative thereof, can be administered to an animal in order to induce the production of sera containing polyclonal antibodies that are capable of binding the chimera.

In a preferred method, antibodies according to the present invention are monoclonal antibodies. Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563–681 (1981)). In general, such procedures involve immunizing an animal with the platelet glycoprotein Ib receptor fragment antigen. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands, J. R., et al. (*Gastroenterology* 80:225–232 (1981). The hybridoma cells obtained through such a selection are then assayed to identify clones which secrete antibodies capable of binding the platelet glycoprotein Ib receptor fragment antigen.

Antibodies according to the present invention also may be polyclonal, or, preferably, region specific polyclonal antibodies.

Antibodies against the adhesion blocking GpIbα platelet receptor fragment according to the present invention are well suited for use in standard immunodiagnostic assays known in the art, including such immunometric or "sandwich" assays as the forward sandwich, reverse sandwich, and simultaneous sandwich assays. The antibodies may be used in any number of combinations as may be determined by those of skill without undue experimentation to effect immunoassays of acceptable specificity, sensitivity, and accuracy for the receptor antigen or equivalents thereof.

Standard reference works setting forth general principles of immunology include Roitt, I., *Essential Immunology*, Sixth Ed., Blackwell Scientific Publications, Publisher, Oxford (1988); Kimball, J. W., *Introduction to Immunology*, Second Ed., Macmillan Publishing Co., Publisher, New York (1986); Roitt, I., et al., *Immunology*, Gower Medical Publishing Ltd., Publisher, London, (1985); Campbell, A., "Monoclonal Antibody Technology," in, Burdon, R., et al., eds., *Laboratory Techniques in Biochemistry and Molecular Biology*, Volume 13, Elsevier, Publisher, Amsterdam (1984); Klein, J., *Immunology: The Science of Self-Nonself Discrimination*, John Wiley & Sons, Publisher, New York (1982); and Kennett, R., et al., eds., *Monoclonal Antibodies, Hybridoma: A New Dimension in Biological Analyses*, Plenum Press, Publisher, New York (1980).

By "detecting" it is intended to include determining the presence or absence of a substance or quantifying the amount of a substance. The term thus refers to the use of the materials, compositions, and methods of the present invention for qualitative and quantitative determinations.

The isolation of other hybridomas secreting monoclonal antibodies of the same specificity as those described herein can be accomplished by the technique of anti-idiotypic screening. Potocmjak, et al., *Science* 215:1637 (1982). Briefly, an anti-idiotypic antibody is an antibody which recognizes unique determinants present on the antibody produced by the clone of interest. The anti-idiotypic antibody is prepared by immunizing an animal of the same strain used as the source of the monoclonal antibody with the monoclonal antibody of interest. The immunized animal will recognize and respond to the idiotypic determinants of the immunizing antibody by producing antibody to these idiotypic determinants (anti-idiotypic antibody).

For replication, the hybrid cells may be cultivated both in vitro and in vivo. High in vivo production makes this the presently preferred method of culture. Briefly, cells from the individual hybrid strains are injected intraperitoneally into pristine-primed BALB/c mice to produce ascites fluid containing high concentrations of the desired monoclonal antibodies. Monoclonal antibodies of isotype IgM or IgG may be purified from cultured supernatants using column chromatography methods well known to those of skill in the art.

Antibodies according to the present invention are particularly suited for use in immunoassays wherein they may be utilized in liquid phase or bound to a solid phase carrier. In addition, the antibodies in these immunoassays can be detectably labeled in various ways.

There are many different labels and methods of labeling known in the art. Examples of the types of labels which can be used in the present invention include, but are not limited to, enzymes, radioisotopes, fluorescent compounds, chemiluminescent compounds, bioluminescent compounds and metal chelates. Those of ordinary skill in the art will know of other suitable labels for binding to antibodies, or will be able to ascertain the same by the use of routine experimentation. Furthermore, the binding of these labels to antibodies can be accomplished using standard techniques commonly known to those of ordinary skill in the art.

One of the ways in which antibodies according to the present invention can be detectably labeled is by linking the antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label antibodies include malate dehydrogenase, staphylococcal nuclease, delta-V-steroid isomerase, yeast alcohol dehydrogenase, α-glycerophosphate dehydrogenase, triose phosphate isomerase, biotin-avidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of detectably labeled antibodies also can be detected by labeling the antibodies with a radioactive isotope which then can be determined by such means as the use of a gamma counter or a scintillation counter. Isotopes which are particularly useful for the purpose of the present invention are $^3H$, $^{125}I$, $^{32}P$, $^{35}S$, $^{14}C$, $^{51}Cr$, $^{36}Cl$, $^{57}Co$, $^{58}Co$, $^{59}Fe$ and $^{75}Se$.

It is also possible to detect the binding of detectably labeled antibodies by labeling the antibodies with a fluorescent compound. When a fluorescently labeled antibody is exposed to light of the proper wave length, its presence then can be detected due to the fluorescence of the dye. Among the most commonly used fluorescent labeling compounds are fluorescein, isothiocyanate, rhodamine, phycoerythrin, phycocyanin, allophycocyanin, o-phthaldehyde and fluorescamine.

The antibodies of the invention also can be detectably labeled using fluorescent emitting metals such as $^{152}Eu$, or others of the lanthanide series. These metals can be attached to the antibody molecule using such metal chelating groups as diethylenetriaminepentaacetic acid (DTPA) or ethylenediaminetetraacetic acid (EDTA).

Antibodies also can be detectably labeled by coupling them to a chemiluminescent compound. The presence of the chemiluminescent-tagged antibody is then determined by detecting the presence of luminescence that arises during the course of the chemical reaction. Examples of particularly useful chemiluminescent labeling compounds are luminol, isoluminol, theromatic acridinium ester, imidazole, acridinium salts, oxalate ester, and dioxetane.

Likewise, a bioluminescent compound may be used to label the antibodies according to the present invention. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labeling include luciferin, luciferase and aequorin.

The antibodies and substantially purified antigen of the present invention are ideally suited for the preparation of a kit. Such a kit may comprise a carrier means being compartmentalized to receive in close confinement therewith one or more container means such as vials, tubes and the like, each of said container means comprising the separate elements of the assay to be used.

The types of assays which can be incorporated in kit form are many, and include, for example, competitive and non-competitive assays. Typical examples of assays which can utilize the antibodies of the invention are radioimmunoassays (RIA), enzyme immunoassays (EIA), enzyme-linked immunosorbent assays (ELISA), and immunometric, or sandwich, immunoassays.

By the term "immunometric assay" or "sandwich immunoassay," it is meant to include simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

In the preferred mode for performing the assays it is important that certain "blockers" be present in the incubation medium (usually added with the labeled soluble antibody). The "blockers" are added to assure that nonspecific proteins, protease, or human antibodies to mouse immunoglobulins present in the experimental sample do not cross-link or destroy the antibodies on the solid phase support, or the radiolabeled indicator antibody, to yield false positive or false negative results. The selection of "blockers" therefore adds substantially to the specificity of the assays described in the present invention.

It has been found that a number of nonrelevant (i.e. nonspecific) antibodies of the same class or subclass (isotype) as those used in the assays (e.g. $IgG_1$, $IgG_{2a}$, IgM, etc.) can be used as "blockers." The concentration of the "blockers" (normally 1–100 microgs/microl) is important, in order to maintain the proper sensitivity yet inhibit any unwanted interference by mutually occurring cross reactive proteins in human serum. In addition, the buffer system containing the "blockers" needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01–10 microgs/ml) to the buffer which contains the "blockers."

There are many solid phase immunoadsorbents which have been employed and which can be used in the present invention. Well known immunoadsorbents include glass, polystyrene, polypropylene, dextran, nylon and other materials, in the form of tubes, beads, and microtiter plates formed from or coated with such materials, and the like. The immobilized antibodies can be either covalently or physically bound to the solid phase immunoadsorbent, by techniques such as covalent bonding via an amide or ester linkage, or by adsorption. Those skilled in the art will know many other suitable solid phase immunoadsorbents and methods for immobilizing antibodies thereon, or will be able to ascertain such, using no more than routine experimentation.

For in vivo, in vitro or in situ diagnosis, labels such as radionuclides may be bound to antibodies according to the present invention either directly or by using an intermediary functional group. An intermediary group which is often used to bind radioisotopes which exist as metallic cations to antibodies is diethylenetriaminepentaacetic acid (DTPA). Typical examples of metallic cations which are bound in this manner are: $^{99m}$Tc, $^{123}$I, $^{111}$IN, $^{131}$I, $^{97}$Ru, $^{67}$Cu, $^{67}$Ga and $^{68}$Ga. The antibodies of the invention can also be labeled with non-radioactive isotopes for purposes of diagnosis. Elements which are particularly useful in this manner are $^{157}$Gd, $^{55}$Mn, $^{162}$Dy, $^{52}$Cr and $^{56}$Fe.

The antigen of the invention may be isolated in substantially pure form employing antibodies according to the present invention. Thus, an embodiment of the present invention provides for substantially pure adhesion blocking GpIbα platelet receptor fragment, said antigen characterized in that it is recognized by and binds to antibodies according to the present invention. In another embodiment, the present invention provides a method of isolating or purifying the adhesion blocking GpIbα platelet receptor fragment antigen, by forming a complex of said antigen with one or more antibodies directed against the adhesion blocking GpIbα platelet receptor fragment.

The substantially pure antigen of the present invention may in turn be used to detect or measure antibody to the adhesion blocking GpIbα platelet receptor fragment in a sample, such as serum or urine. Thus, one embodiment of the present invention comprises a method of detecting the presence or amount of antibody to the adhesion blocking GpIbα platelet receptor fragment antigen in a sample, comprising contacting said sample containing said antibody to the platelet glycoprotein Ib receptor fragment antigen with detectably labeled adhesion blocking GpIbα platelet receptor fragment, and detecting said label. It will be appreciated that immunoreactive fractions and immunoreactive analogues of the fragment also may be used. By the term "immunoreactive fraction" is intended any portion of the platelet glycoprotein Ib receptor fragment antigen which demonstrates an equivalent immune response to an antibody directed against the receptor chimera. By the term "immunoreactive analogue" is intended a protein which differs from the receptor fragment by one or more amino acids, but which demonstrates an equivalent immunoresponse to an antibody of the invention.

The pharmaceutical compositions of the invention may be administered to any animal which may experience the beneficial effects of the compounds of the invention. Foremost among such animals are humans, although the invention is not intended to be so limited.

The manner and method of carrying out the present invention may be more fully understood by those of skill by reference to the following examples, which examples are not intended in any manner to limit the scope of the present invention or of the claims directed thereto.

EXAMPLE I

Construction of Deletion Mutants

Figure 1:
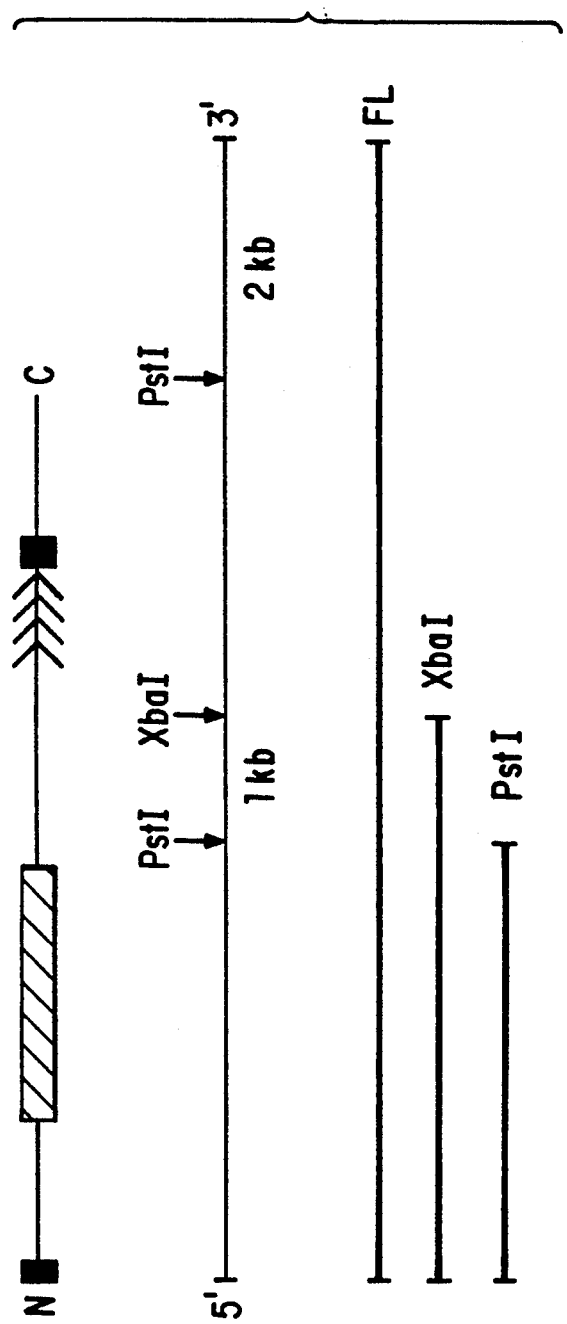
FIG. 1—Organization of the GpIbα polypeptide and cDNA and strategy for construction of deletion mutants. The top line depicts the major structural features of the GpIbα polypeptide. The solid box represents the highly hydrophobic signal peptide and transmembrane domains. The hatched box marks the location of the 8 contiguous leucine-rich repeats, and the arrowheads delineate the serine-threonine rich region of the polypeptide which is the predicted site for 0-linked oligosaccharide attachment. The second line depicts a partial restriction map of GpIbα cDNA and, below it, maps for the three deletion mutants that were ligated into pCDM8 for transient expression in COS 7 cells.

Full length GpIbα cDNA was obtained by screening a megakaryocytic cDNA library constructed from mRNA prepared from a megakaryocytic cell line (DAMI) which expresses GpIb/IX (Greenberg, S. M., et al., *Blood* 72:1968–1977 (1988)). The library was screened with a partial GpIbα cDNA kindly provided by Drs. Jose Lopez and Gerry Roth, University of Washington, Seattle. Full length cDNA was then assembled in the plasmid vector pGEM4 and sequenced by the double stranded dideoxy technique (Chen, E. Y., et al., *DNA* 4:165–170 (1985)). The sequence obtained was identical to that published by Lopez et al. (Lopez, J. A., et al., *Proc. Natl. Acad. Sci. U.S.A.* 84:5615–5619 (1987)). The cDNA was then subcloned into the eukaryotic expression plasmid CDM8 provided by Dr. Brian Seed at the Massachusetts General Hospital, Boston Mass. to produce pCDM8-GpIbα. The CDM8 vector contains a cloning site downstream from the cytomegalovirus promoter as well as the SV40 origin of replication, permitting transient expression of the heterologous protein in COS cells (Aruffo, A., et al., *Proc. Natl. Acad. Sci. U.S.A.* 84:8573–8577 (1987)). The deletion mutants were constructed by digesting pCDM8-GpIbα with Xba 1, filling in the 5' overhang with the Klenow fragment of DNA polymerase and religating the truncated cDNA to yield pCDM8-GpIbαXbaI (FIG. 1). A second deletion mutant was constructed by partial digestion with Pst 1 to preferentially digest a Pst 1 site at nucleotide 750 in the cDNA sequence. The 3' overhang was then digested with T7 polymerase and the appropriate band purified on 1% agarose, extracted, precipitated and religated to yield pCDM8-GpIbαPstI.

COS-7 Cell Transfection

The three GpIbα expression plasmids were transfected into COS-7 cells using the DEAE dextran method of Aruffo and Seed (Aruffo, A., et al., *Proc. Natl. Acad. Sci. U.S.A.* 84:8573–8577 (1987)). Briefly, subconfluent cell monolayers that had been grown on 10 cm Petri dishes (Falcon Plastics) were washed with 10 ml phosphate-buffered saline (PBS) and covered with 2 ml of Dulbeco's modified essential medium (DMEM) supplemented with 10% NuSerum (Collaborative Research, Lexington, Mass.) and 100 μM chloroquine diphosphate (Sigma Chemicals) (transfection medium). Two μg of each plasmid to be transfected was then added to a dish of COS cells followed by the slow addition of 0.5 ml of a 2 μg/ml solution of DEAE-dextran (Pharmacia LKB Biotechnology Inc.) made up in transfection medium. After 4 h incubation at 37° C., the transfection medium was removed and the cells were incubated in 2 ml of 10% dimethyl sulfoxide in PBS for 2 minutes. The cells were then washed with PBS and incubated in 10 ml DMEM supplemented with 10% fetal calf serum at 37° C. in a 10% CO$_2$ atmosphere for 48–72 hours.

Radiolabeling

After 48–72 hours, the conditioned medium was removed and the cells washed with PBS and then incubated for 1 h in cysteine/methionine free DME supplemented with 20 mM HEPES. The cells were then incubated for varying time periods with 0.5 mCi [$^{35}$S]-methionine (New England Nuclear, Boston, Mass.) and the cells and conditioned medium harvested separately for subsequent immunoprecipitation and analysis of radiolabeled proteins. For pulse-chase studies, 1 mM nonradioactive methionine was added after one hour of radiolabeling with [$^{35}$S]-methionine.

Immunoprecipitation

COS cell monolayers were lysed on ice by the addition of 1 ml of a solution containing 20 mM Tris-HCl, pH 7.6, 150 mM NaCl, 1% digitonin, 0.12% Triton X-100, 10 mM iodoacetamide, 1 mM phenylmethylsulfonyl fluoride and 1 mg/ml each of leupeptin, pepstatin, aprotinin. After a 30 minute incubation, the cell lysates were centrifuged at 13,000×g for 15 minutes at 4° C. to remove particulate matter. Cell lysates and conditioned medium were then "pre-cleared" by incubation with preformed rabbit anti-mouse goat anti-rabbit immune complexes for 12-18 hours with constant agitation at 4° C. The immunoprecipitate was sedimented by centrifugation at 13,000×g for 10 minutes. After two or three cycles of "pre-clearing", the cell lysate or conditioned medium was incubated overnight with mouse anti-GpIbα monoclonal antibody 6D1, or monoclonals AS-2 and AS-7. These three antibodies recognize epitopes on GpIbα that are present in the glycocalicin portion of the molecule (Coller, B. S., et al., Blood 61:99-110 (1983); Miller, J. L., et al., Br. J. Haematol. 74:313-319 (1990)). The epitopes are thought to lie near the vWF binding site as incubation of platelets with all three of these antibodies inhibited ristocetin-dependent binding of vWF and ristocetin-dependent platelet agglutination. The immunoprecipitates were collected by centrifugation at 13,000×g for 10 minutes and washed 7 to 9 times in the previously described lysis buffer. The washed immunoprecipitates were then analyzed by SDS-PAGE using 5% polyacrylamide gels according to the technique of Laemmli (Laemmli, U. K., Nature 227:680-685 (1970)). A polyclonal rabbit antibody against GRP78 (BIP) was also used.

The gels were prepared for autoradiography by enhancement with Omnifluor (New England Nuclear, Boston Mass.). Autoradiography was carried out for 24-72 hours at −80° C. with Kodak XAR-2 film and one intensifying screen. In some experiments samples were transferred to nitrocellulose by Western blotting and incubated with rabbit anti-human GpIbα followed by [$^{125}$I]-goat antirabbit second antibody, as previously described (Vicente, V., et al., J. Biol. Chem. 274-280 (1990)).

Purification and Radiolabeling of vWF vWF was purified from outdated human cryoprecipitate obtained from the Northeast Regional Red Cross. A previously described method which utilizes differential precipitation with ammonium sulfate and gel filtration on Sephacryl 51000 (Bockenstedt, P., et al., J. Clin. Invest. 78:551-556 (1986)) was used. Purified vWF was analyzed by SDS-PAGE (Laemmli, U. K., Nature 227:680-685 (1970) and by SDS-agarose gel electrophoresis (Wise, R. J., et al.. Cell 52:229-236 (1988)) and contained the expected 220,000 Mr vWF subunit polypeptide and the full spectrum of multimers present in unfractionated plasma. vWF was radiolabeled with Iodo Beads (Pierce Chemicals, Rockford Ill.) using a previously described technique (Laemmli, U. K., Nature 227:680-685 (1970)). The specific activity of the [$^{125}$I]-vWF was between 0.75 and 1 μCi/μg protein.

Inhibition of vWF Binding

The ability of recombinant GpIbα (rGpIbα) to inhibit ristocetin-dependent binding of [$^{125}$I]-vWF to platelets was assessed with paraformaldehyde-fixed platelets (Allain, J. P., et al., J. Lab. Clin. Med. 85:318-328 (1975)). The platelets were washed free of plasma by repeated centrifugation. A 100 μl suspension of 1×10$^8$ platelets/ml in TBS (10 mM Tris HCl 150 mM NaCl, pH 7.5) containing 5 μCi [$^{125}$I]-vWF and the ligand was incubated at 25° C. Binding was initiated by the addition of a final concentration of 1 mg/ml ristocetin and incubation continued for 60 minutes. Platelet-bound vWF was separated from unbound vWF by centrifugation of the platelet suspension through a 500 μl cushion of 5% sucrose gradient at 13,000×g for 10 min at 4° C. The ability of purified GC or the rGpIbα polypeptides to block vWF binding was assessed by adding increasing concentrations of the appropriate test substance to the assay mixture. GC was purified, as previously described, from outdated human platelet concentrates (Michelson, A. D., et al., Blood 67:19-26 (1986)). Conditioned medium from COS cells was harvested, concentrated 10-50 fold either by ultrafiltration or by dialysis into 10 mM Tris, pH 8.0 followed by lyophilization. The concentration of GC or rGpIbα was assessed using a previously described ELISA employing either a polyclonal rabbit anti-GpIb antibody or the mouse monoclonal 6D1 (Michelson, A. D., et al., Blood 67:19-26 (1986)). In some experiments the concentrated conditioned medium was incubated with 100 HM dithiothreitol for 1 hour at 25° C. followed by an additional hour with a 10 fold excess of iodoacetamide. The reduced and alkylated conditioned medium was dialyzed one additional time against 10 mM Tris, pH 8.0 prior to use in the binding assays.

RESULTS

Following transfection of COS cells with an expression plasmid containing the full length GpIbα cDNA (pCDM8-GpIbαFL), a 48/46 kDa doublet was immunoprecipitated from COS cell lysates with the monoclonal antibody 6D1. Both of the proteins in the doublet were smaller than the 57 kDa product predicted by the open reading frame in the full length cDNA. A doublet with the same electrophoretic mobility was also detected in the COS cell conditioned medium following transfection with the full length expression plasmid. The intracellular processing and secretion of recombinant GpIbα (rGpIbα) was then studied by metabolic labeling over a 24 hour period. A pulse-chase analysis of radiolabeled rGpIbα polypeptides following COS cell transfection is shown in FIG. 3. There was maximum accumulation of product at 2 hours, with a slow decline over the next 24 hours. There was also a reciprocal increase in the amount of radiolabeled 48/46 kDa doublet secreted into COS cell conditioned medium with progressive accumulation of radiolabelled rGpIbα polypeptides over the 16 hours of observation (FIG. 3).

Also detected were increasing quantities of a doublet with identical electrophoretic mobility in COS cell conditioned medium following transfection with a plasmid containing GpIbα cDNA truncated at its single Xba I site (pCDM8-GpIbαXbaI). This deletion terminated translation of the full length GpIbα cDNA at leucine 318 yielding the polypeptide rGpIbαL$_{318}$. Following transfection with this plasmid, the majority of the radiolabeled product could be immunoprecipitated from the conditioned medium and little was retained within the COS cells. [$^{35}$S]-methionine labeled polypeptide was readily detected one hour after labeling, with steady accumulation of radiolabeled protein in the medium for at least 16 hours after pulse labeling.

The potential role of N-linked glycosylation in doublet formation was investigated by incubation of rGpIbα polypeptides with endoglycosidase F prior to immunoprecipitation and electrophoresis. Following transfection of COS cells with either pCDM8-GpIbαFL or pCDM8-GpIbαXbaI, conditioned medium to which endoglycosidase F had been added no longer contained a doublet, but had a single radioactive protein band with increased electrophoretic mobility. The estimated Mr of the N deglycosylated polypeptide produced by incubation with endoglycosidase F was 37 KDa which is in close agreement with the predicted size for a 318 amino acid polypeptide of 34.9 kDa. The product obtained from both transfections had identical electrophoretic mobility suggesting that the polypeptides were quite similar.

In contrast to the results obtained after transfection with pCDM8-GpIbαXbaI, transfection with pCDM8-GpIbαPstI, which had an additional 294 nucleotides deleted, produced a protein which no longer could be immunoprecipitated by 6D1 (FIG. 1, lane 4). A similar pattern was seen following immunoprecipitation of all three rGpIbα polypeptides with two additional monoclonal antibodies AS-2 and AS-7. These two antibodies precipitated the identical 48/46 kDa doublet from COS cell lysates and conditioned medium following transfection with pCDM8-GpIbαFL or pCDM8-GpIbαXbaI but could not precipitate any radiolabeled product following transfection with pCDM8-GpIbαPstI. These data suggested that at least part of the epitope(s) recognized by 6D1, AS-2 and AS-7 was located between leucine 220 and leucine 318.

In order to document that rGpIbαL$_{220}$ encoded a truncated GpIbα polypeptide, an aliquot of conditioned medium was transferred onto nitrocellulose by Western blotting and incubated with a polyclonal rabbit anti-human glycocalicin antibody. A band of appropriate mobility was detected following transfection with pCDM8-GpIbαL$_{318}$ or pC0M8-GpIbαL$_{220}$. However, no band was detected following transfection with non-recombinant pCDM8 or with pCDM8 containing GpIbα cDNA in the reverse (non coding) orientation.

To demonstrate that the rGpIbα polypeptides which contained epitopes reacting with 6D1, AS-2 and AS-7 could block ristocetin-dependent binding of vWF to platelets, conditioned medium from 10 dishes of COS cells transfected with either pCDM8-GpIbαXbaI or pCDM8-GpIbαPst1 was pooled and dialyzed into 10 mM Tris pH 8.0 and then lyophilized and concentrated 10–50 fold. The concentrated, dialyzed medium was then used as a competitor in radioligand binding assays. As shown in FIG. 3, the polypeptide produced by transfection of the plasmid containing cDNA truncated at the Xba 1 site (rGpIbαL$_{318}$) inhibited the ristocetin-dependent binding of [$^{125}$I]-vWF to fixed washed platelets. In contrast, the rGpIbαL$_{220}$ polypeptide could not inhibit [$^{125}$I]-vWF binding. The I.C.$_{50}$ for rGpIbαL$_{318}$ was approximately 20 nM and is identical to the I.C.$_{50}$ for purified glycocalicin derived from human platelets. Next looked at were the effects of N-deglycosylation with endoglycosidase F on the biological activity of the recombinant polypeptide. Removal of sufficient carbohydrate with endoglycosidase F to eliminate the doublet form of the protein and increase the electrophoretic mobility of rGpIbαL$_{318}$ did not change the I.C.$_{50}$ in the radioligand binding assay (FIG. 3). In contrast disulfide bond reduction with dithiothreitol and alkylation with iodoacetamide completely abolished activity in the same assay (FIG. 3).

DISCUSSION

This example has demonstrated that COS cells transfected with cDNAs encoding GpIbα, one of the three chains in the GpIb/IX complex, express truncated, but biologically active, rGpIbα polypeptides. Transfection with full length GpIbα cDNA yielded a polypeptide doublet of 48/46 kDa. The doublet was substantially smaller than the 57.5 kDa product predicted for the non-glycosylated protein theoretically encoded by the full length cDNA. Transfection with a cDNA truncated at a naturally occurring Xba 1 site (pCDMS-GpIbαXbaI), also yielded a polypeptide doublet with identical electrophoretic mobility. Intracellular processing of the recombinant polypeptide was slower than anticipated with distribution of protein both inside the cells and in the conditioned medium. Finally, the recombinant doublet could be resolved into a single band, with an estimated molecular weight of 37 kDa, following digestion with endoglycosidase F. Some of the cleaved polypeptide was then secreted into the conditioned medium and a second fraction was retained in the endoplasmic reticulum and processed over 8 to 12 hours. It is not surprising that transfection with a cDNA encoding only one half of the GpIbα, heterodimer produced a polypeptide that was retained in the endoplasmic reticulum. It would be unlikely for the primary translation product of the GpIbα cDNA to be folded properly without co-expression of GpIb and GpIX. In fact, it was possible to immunoprecipitate the intracellular rGpIbα polypeptide doublet with an antibody to GRP78, a resident endoplasmic reticulum protein which binds improperly folded polypeptides (Lodish, H., *J. Biol. Chem.* 263:8573–8577 (1988)).

Fortunately, however, a fraction of each truncated polypeptide was released following its proteolysis and the secreted polypeptides retained biological activity. This suggests that at least the vWF binding region of rGpIbα produced in COS cells is properly folded and can assume a native conformation. Since monoclonal antibodies which recognize epitopes near the vWF binding site also immunoprecipitated the retained intracellular rGpIbα polypeptides, the vWF binding region must also be properly folded in the polypeptide fraction retained in the endoplasmic reticulum.

These expression studies in a heterologous cell provided a means to analyze the potential role of carbohydrate in the GpIb-vWF interaction. Since 50% of the mass of the GpIbα polypeptide is carbohydrate, initially it was assumed that either N-linked or 0-linked oligosaccharides would play some role in vWF binding. In previous studies it was demonstrated that enzymatic removal of 0-linked oligosaccharide chains impaired the interaction of glycocalicin with both 6D1 and vWF (Michelson, A. D., et al., *Blood* 67:19–26 (1986)). None of the recombinant polypeptides analyzed here contained the serine, threonine-rich region to which 0-linked oligosaccharides of GpIbα are attached. However, the biologic activity of rGpIbαL$_{318}$, as measured by inhibition of ristocetin-dependent binding of [$^{125}$I]-vWF to platelets, was identical to that of platelet glycocalicin, a larger proteolytic fragment of the native receptor which contains the glycosylated.

In addition, two of the four potential N-linked glycosylation sites in GpIbα are within the sequence expressed in the three recombinant polypeptides. They are located at asparagines 21 and 159 (Lopez, J. A., et al., *Proc. Natl. Acad. Sci. U.S.A.* 84:5615–5619 (1987)). Presumably, incomplete glycosylation at these two sites accounted for the observed doublet formed by the recombinant polypeptides as well as the anomalous electrophoretic mobility by SDS-PAGE. Enzymatic cleavage of N-linked carbohydrate at these two sites eliminated the doublet and increased electrophoretic mobility. This reduced the apparent Mr by approximately 10,000 daltons, bringing the estimate quite close to the Mr of 37.5 kDa predicted from the primary sequence.

The deletion mutants have also provided new information about the vWF binding site on GpIbα. Two previous studies employing synthetic peptides had localized the interaction site to a region between serine 215 and tyrosine 279 (Vicente, V., et al., *J. Biol. Chem.* 265:274-280 (1990); Katagiri, Y., et al., *Thromb. Haemst.* 63:122-126)). However, the concentrations of peptide needed to inhibit ristocetin or botrocetin-induced binding of vWF to platelets was much higher than the concentrations of GC used in previous studies (Michelson, A. D., et al., *Blood* 67:19-26 (1986); Vicente, V., et al., *J. Biol. Chem.* 265:274-280 (1990); Katagiri, Y., et al., *Thromb. Haemst.* 63:122-126)).

The rGpIbα polypeptides produced here, which contain the region encompassed by the synthetic peptides, are as effective as GC in inhibiting the ristocetin-mediated interaction of vWF with platelet GpIb/IX. The present studies also clearly demonstrate that deletion of the sequence between leucines 221 and 318 eliminates interaction with three monoclonal antibodies—6D1, AS-2 and AS-7. The same deletion which creates rGpIbαL$_{220}$, also abolishes the inhibition of the ristocetin-induced binding of vWF to platelets. Disulfide reduction also abolishes these interactions suggesting a conformation-sensitive disulfide in the vWF binding region of GpIbα. The most likely candidate would be an interchain disulfide bond between cysteines 248 and 264. However, there are four other cysteines present in the rGpIbα polypeptides expressed here, and the possibility that reduction of more distant disulfide bonds might secondarily perturb the vWF binding site cannot be excluded.

The results disclosed in this example demonstrate that it is possible for a heterologous cell to produce a properly folded biologically active molecule after transfection with just one of the three polypeptide chains that constitute the GpIb/IX complex. The truncated soluble rGpIbα polypeptides produced here provide agents capable of perturbing shear-dependent platelet adhesion by inhibiting the vWF-platelet interaction.

EXAMPLE II

Vector Construction and Expression

The expression vector, pT7-7 (Tabor, S., et al., *Proc. Natl. Acad. Sci. U.S.A.* 82:1074-1078 (1985)), which contains the T7 RNA polymerase promoter, a convenient polylinker for cloning, and which confers ampicillin resistance, was digested with Hind III and Pst 1 and the 5' overhang filled in with T4 DNA polymerase. A 289 by cDNA fragment was isolated from full length GpIbα cDNA in pUC19 by digestion with Xba 1 and Pst 1. The 5' overhang at the Xba 1 site was filled in by incubation with T4 DNA polymerase and the fragment purified from a low melting point agarose gel and ligated into blunt-ended, Pst 1-digested pT7-7 to yield pT7GpIbα. The recombinant plasmid was then used to transform *E. coli* K38 strain pGP1-2, which contains plasmids encoding the T7 RNA polymerase and kanamycin resistance genes. Transformed cells were selected on LB plates incubated at 30° C. that contained 75 μg/ml each of ampicillin and kanamycin. A map of the vector and the strategy employed for expression vector construction are shown in FIG. 4. The protein encoded by this cDNA fragment includes GpIbα residues glutamine 221 through leucine 318 (rGpIbαQ$_{221}$-L$_{318}$). As shown in FIG. 4, there are an additional 10 amino terminal and 16 carboxy terminal amino acids of vector sequence added to the recombinant polypeptide.

Expression and Purification of Recombinant GPIbα

To express the recombinant protein, *E. coli* K38 strain pGP1-2 containing pT7GpIbα was cultured overnight at 30° C. in 3 liters of 2% tryptone/1% yeast extract/2% NaCl, pH 7.4, and 50 μg/ml each of ampicillin and kanamycin. The T7 RNA polymerase promoter was then derepressed by raising the culture temperature to 42° C. for 4 hours. The cells were harvested and resuspended in 60ml of lysis buffer (50mM Tris-HCl, 0.1 M NaCl, 1 mM EDTA, pH 8.0) containing a final concentration of 250 μg/ml lysozyme, and allowed to stand for 1 hour at 4° C. The lysate was sonicated for 1 to 2 minutes and centrifuged at 48,000×g for 30 minutes. The resultant pellet was resuspended with 0.8% SDS and 100 μM β-mercaptoethanol by constant stirring overnight at 4° C. The resuspended material was centrifuged at 48,000 g for 30 minutes and the supernatant was slowly dialyzed against 0.1 M Tris-HCl, pH 8.0. This solution was passed over affinity columns prepared with either of two monoclonal antibodies (AS-7 and 6D1) that were coupled to an Amino Link column (Pierce Chemicals, Rockford Ill.) Both antibodies recognize epitopes on GpIbα that are at or near the vWF binding site (Coller, B. S., et al., *Blood* 61:99-110 (1983); Miller, J. L., et al., *Br. J. Haematol.* 74:313-319 (1990)). After equilibration for 1 to 2 hours, retained protein was eluted with 0.15 M NaCl, adjusted to pH 11.0 with concentrated NH$_4$OH, immediately dialyzed against TBS (20 mM Tris-HCl, 0.15 M NaCl, pH 7.4), and then concentrated by lyophilization. The purified material was then resuspended in and dialyzed against additional TBS and stored at −20° C.

Purification of vWF vWF was purified by two methods. For platelet aggregation studies, vWF was purified from cryoprecipitated human plasma using an affinity column containing a monospecific polyclonal rabbit anti human vWF antibody coupled to a Amino Link column. vWF bound to the antibody column was eluted with 3M NaSCN in TSE (20 mM Tris-HCl, 20 mM sodium citrate, 20 mM aminocaproic acid, pH 7.0). The eluate was dialyzed against TBS and concentrated by ultrafiltration with an Amicon PM-30 membrane (Amicon Corp., Lexington Mass.).

For the binding studies, vWF was purified from cryoprecipitate using a previously described method which utilizes differential precipitation with ammonium sulfate and gel filtration on Sephacryl 51000 Bockenstedt, P., et al., *J. Clin. Invest.* 78:551-556 (1986)). Both preparations were analyzed by SDS-PAGE and by SDS-agarose gel electrophoresis and both contained the expected 220,000 Mr vWF subunit polypeptide and the full spectrum of multimers present in unfractionated plasma.

Platelet Aggregation

Platelet aggregation was carried out in siliconized glass cuvettes at 37° C. with constant stirring at 1,200 rpm in a four channel aggregometer. Aggregation of a 3×10$^8$/ml suspension of paraformaldehyde fixed platelets containing 5 to 10 μg/ml purified vWF and increasing concentrations of rGPIbα$_{221}$-L$_{318}$ was initiated by the addition of a final concentration of 1.5 mg/ml ristocetin to the cuvette.

vWF Binding to Platelets and Collagen

Inhibition of vWF binding to platelet GpIb/IX was also measured with washed, paraformaldehyde-fixed platelets (Allain, J. P., et al., *J. Lab. Clin. Med.* 85:318-328 (1975)). A final concentration of $1\times10^8$ platelets/ml was incubated in TBS buffer containing 5 μg/ml [$^{125}$I]-vWF and increasing concentrations of rGPIbαQ$_{221}$-L$_{318}$. Binding was initiated by the addition of 1 mg/ml final concentration ristocetin. After 30 minutes incubation at 25° C, platelet bound ligand was separated from free ligand by centrifuging 50 μl of the mixture through a cushion of 500 μl 50% sucrose, at 12,000×g for 4 minutes. The supernatant was carefully aspirated and radioactivity associated with the platelet pellet was measured in a gamma spectrometer. Non-specific binding was evaluated by adding a 35-fold excess of non-radioactive vWF and by carrying out parallel incubations without ristocetin. Non-specific binding under both conditions averaged 20-25% of total binding. For studying inhibition of vWF binding to GpIIb/IIIa, freshly collected platelets were washed free of vWF and other plasma proteins by gel filtration on a Sepharose 2B column followed by centrifugation on an albumen density gradient (Allain, J. P., et al., *J. Lab. Clin. Med.* 85:318-328 (1975)). The concentration of platelets, [$^{125}$I]-vWF, rGpIbαQ$_{221}$-L$_{318}$ and conditions for incubation and separation of bound from free ligand were as described above. Binding was initiated by the addition of 10 μM ADP.

Inhibition of vWF binding to collagen was assessed with a previously described technique (Bockenstedt, P., et al., *J. Clin. Invest.* 78:551-556 (1986)). Briefly, a final concentration of 1.87 mg/ml acid-soluble Types I and III calf skin collagen was added to microtiter wells in 20 mM citrate buffer, pH 6.1 for 90 minutes. After washing several times with TBS to remove non-adsorbed collagen, non-specific binding sites were blocked by the addition of 1 mg/ml Bovine Serum Albumin (BSA) to each well for 60 minutes. A final concentration of 10 μg/ml [$^{125}$I]-vWF was added to the collagen-coated microtiter wells along with increasing concentrations of rGpIbα polypeptide and incubated for 30 minutes at 25° C. Wells were washed with 1 mg/ml BSA in TBS and the radioactivity remaining in each well measured. Non-specific binding was evaluated by adding a 35-fold excess of unlabeled ligand and amounted to 15-20% of total binding. In some experiments, the binding of rGpIbαQ$_{221}$-L$_{318}$ to collagen was assessed by incubating increasing concentrations of radiolabeled polypeptide to collagen-coated microtiter wells.

vWF Binding to rGpIbαQ$_{221}$-L$_{318}$

A solid phase ligand binding assay was developed by adsorbing solubilized bacterial lysate containing the recombinant protein onto Immobilon membranes (Millipore Corp., Bedford, Mass.). The bacterial extracts were diluted in electroblotting buffer (0.02 M Tris-Glycine-15% methanol). The membranes were then soaked in 5% fat free skim milk at 4° C. for several hours, washed in TBS, 0.05% Tween-20 (TBS-T), and incubated overnight at 25° C. in TBS-T buffer containing 5 μg/ml [$^{125}$I]-vWF The membranes were then washed in several changes of TBS-T, air dried and prepared for autoradiography for 1-2 hours at −80° C. using Kodak vAR-2 film and one intensifying screen. Non-specific binding was assessed by including lanes containing non-recombinant pT7-7.

SDS polyacrylamide gel electrophoresis (SDS-PAGE) was performed by the method of Laemmli (Laemmli, U. K., *Nature* 227:680-685 (1970)). SDS-agarose gel electrophoresis was carried out using a previously described technique (Wise, R. J., et al., *Cell* 52:229-236 (1988)). Protein concentration was determined by the BCA method (Pierce Chemicals, Rockford Ill.). Plasmid constructions and recombinant DNA techniques used standard protocols. [$^{125}$I]-vWF and [$^{125}$I]-rGpIbαQ$_{221}$-L$_{318}$ were prepared, as previously described, with the Iodo-Bead technique (Pierce Chemicals, Rockford Ill.) (Bockenstedt, P., et al., *J. Clin. Invest.* 78:551-556 (1986)). Radiolabeled proteins were separated from unincorporated radioactivity by centrifugation through a Centri/Por filter (Spectrum Corp.). The specific activity of [$^{125}$I]-vWF was 0.72 μCi/μg and [$^{125}$I]-rGpIbαQ$_{221}$-L$_{318}$ 0.90 μCi/μg.

Results

Although there are a large number of vectors available for expressing heterologous proteins in *E. coli*, pT7-7 was chosen because of the potential for efficient expression of a recombinant protein without the need to create a large bacterial fusion protein. After heat shock to derepress the T7 RNA polymerase promoter, the transformed cells produced a single new band of appropriate molecular weight. The calculated molecular weight for the sequence between glutamine 221 and leucine 318 is 10,670. The 26 additional amino acids from the vector sequence add another 2970 daltons bringing the Mr to 13,640. This agrees closely with the estimate from 12% SDS-PAGE of 16,000. In addition, *E. coli* K38 containing pGpIbα that were incubated in media containing [$^{35}$S]-methionine and rifampicin to block endogenous RNA polymerase activity synthesized only one radiolabeled product of identical molecular weight. The radiolabeled protein had a T$_½$ of 20 minutes by pulse-chase analysis.

Since the expression vector did not contain an appropriate bacterial leader sequence to facilitate secretion into the bacterial periplasm, rGpIbαQ$_{221}$-L$_{318}$ was retained within the bacteria after synthesis and sedimented with insoluble organelles. However, extracts of bacteria containing the recombinant polypeptide could bind [$^{125}$I]-vWF as shown in FIG. 3. This suggested that the protein produced in *E. coli* was in a native or near native conformation. The protein could also be readily solubilized in 0.8% SDS and 100 μM β-mercaptoethanol and then adsorbed to and eluted from monoclonal affinity columns. This provided a simple method to purify the protein to homogeneity.

Inhibition of vWF binding to platelet GpIb/IX by rGpIbαQ$_{221}$-L$_{318}$ was assessed in two ways. First, the inhibition of ristocetin-dependent binding of [$^{125}$I]-vWF to fixed washed platelets was examined. rGpIbαQ$_{221}$-L$_{318}$ blocked [$^{125}$I]-vWF binding to fixed washed platelets in a dose-dependent manner with an I.C.$_{50}$ of 450 nM. Second, similar concentrations of soluble rGpIbαQ$_{221}$-L$_{318}$ inhibited ristocetin-dependent platelet agglutination (FIG. 7). Fifty percent inhibition of agglutination required 500 nM recombinant GpIbα polypeptide. Finally, reduction and alkylation of the rGpIbα polypeptide abolished its ability to inhibit ristocetin-dependent binding of vWF to platelets (FIG. 6). Since there are only two cysteine residues in the recombinant polypeptide, this is strong evidence that a disulfide bond between cysteines 248 and 264 is needed to maintain rGpIbaQ$_{221}$-L$_{318}$ in its native conformation and to preserve its biologic activity.

rGpIbaQ$_{221}$-L$_{318}$ clearly inhibited ristocetin-dependent vWF binding to GpIb/IX. In order to determine whether the fragment could bind to vWF in the absence of ristocetin, a solid phase binding assay was developed. As previously shown in FIG. 3, [$^{125}$I]-vWF bound to bacterial extracts induced to synthesize rGpIbaQ$_{221}$-L$_{318}$ that had been immobilized on a membrane. This suggests a direct interaction between the recombinant polypeptide and vwF.

The ability of the GpIba chain polypeptide to block the binding of vWF to other vWF receptor sites on the platelet was then examined. As shown in FIG. 8, concentrations of rGpIbaQ$_{221}$-L$_{318}$ which inhibited [$^{125}$I]-vWF binding to platelet GpIb/IX did not inhibit ADP-induced binding to fresh washed platelets. It is not surprising that rGpIbaQ$_{221}$-L$_{318}$ did not block vWF binding to platelet GpIIb/IIIa, as the consensus adhesive protein sequence (RGD), which mediates binding to GpIIb/IIIa, is located some distance from the GpIb/IX interaction site of vWF at amino acid residues 1744–1747 of the mature vWF subunit (Bonthron, D. T., et al., *Nucleic Acids Res.* 14:7125–7127 (1986)).

Next examined was the effect of rGpIbaQ$_{221}$-L$_{318}$ on a third interaction—the binding of vWF to type I and III collagen fibrils. As shown in FIG. 9, rGpIbaQ$_{221}$-L$_{318}$ competed effectively with [$^{125}$I]-vWF and prevented bindign to a mixture of insolubilized Type I and III collagen fibrils formed in situ in the microtiter wells. Inhibition of [$^{125}$I]-vWF binding was dose-dependent, with an I.C.$_{50}$ of 200 nM rGpIbaQ$_{221}$-L$_{318}$. Furthermore, inhibition of vWF binding to collagen by the polypeptide did not require addition of ristocetin. In order to determine whether the GpIba fragment prevented vWF binding to collagen by competing for potential vWF binding sites on the insolubilized collagen fibrils, increasing concentrations of [$^{125}$I]-rGpIbaQ$_{221}$-L$_{318}$ were added to collagen-coated microtiter wells. In contrast to [$^{125}$I]-vWF, almost no radiolabeled rGpIba adhered to the collagen fibrils. Following incubation with a final concentration of 3kn [$^{125}$I]-rGpIbaQ$_{221}$-L$_{318}$ only.0.1 pmole ligand bound to either the collagen coated or BSA coated wells. With lower concentrations of radiolabeled rGpIbd, binding was not above background.

Discussion

The recombinant polypeptide, rGpIbaQ$_{221}$-L$_{318}$, a hydrophilic fragment of the GpIba chain which retains biologic activity in several in vitro assays, has been expressed. This recombinant polypeptide: 1) effectively prevents vWF binding to the platelet GpIb/IX complex; 2) inhibits ristocetin-dependent platelet agglutination; 3) inhibits vWF binding to collagen coated surfaces; 4) does not prevent the binding of vWF to platelet GpIIb/IIIa; 5) binds to GpIb/IX recognition sites on vWF multimers with high affinity and; 6) requires a disulfide bond between cysteines 248 and 264 for biologic activity. The pT7-7 expression vector employed here permitted expression of a recombinant polypeptide that was readily solubilized and purified. The small size, 13,640 daltons, absence of N-linked or 0-linked carbohydrate, and the presence of only two cysteine residues in the sequence between glutamine 221 and leucine 318 made this a potentially favorable region of GpIba to express in *E. coli*. Although numerous methods for protein purification could have been utilized, monoclonal antibody chromatography was chosen to assure that the purified species would be in a native conformation and, hopefully, would retain its biologic activity. The two monoclonal antibodies used to construct the affinity columns, AS-7 and 6D1, were chosen because they both recognized epitopes near the vWF interaction site (Coller, B. S., et al., *Blood* 61:99–110 (1983); Miller, J. L., et al., *Br. J. Haematol.* 74:313–319 (1990)). It has also been shown that both of these antibodies could immunoprecipitate recombinant GpIba polypeptides expressed in COS cells which contained the sequence expressed in rGpIbaQ$_{221}$-L$_{318}$ (Petersen, E., et al., *J. Biol. Chem.* (submitted)). At the time the solubilization and purification procedure was being developed, the critical role of the disulfide bond linking cysteines 248 and 264 was not fully appreciated. It is now thought that the inclusion of mercaptoethanol in an early purification step to help solubilize inclusion bodies may have lowered the subsequent yield obtained from affinity purification by unfolding the recombinant protein. Following incubation with β-mercaptoethanol, successful affinity purification required proper refolding of the protein into a native conformation and reformation of the single disulfide bond.

This example both confirms and extends two previous reports which employed synthetic peptides spanning portions of the sequence expressed in [rGpIbaQ$_{221}$-L$_{318}$ to inhibit vWF binding to platelet GpIb/IX. Vicente and colleagues first reported that a synthetic peptide spanning serine 215 to tyrosine 279 inhibited both ristocetin- and botrocetin-induced binding of vWF to platelets, while a shorter peptide containing glycine 271 to glutamine 285 was a less potent inhibitor (Vicente, V., et al., *J. Biol. Chem.* 265:274–280 (1990)). Katagiri et al. then reported that a synthetic peptide spanning amino acid residues aspartate$_{235}$ to lysine$_{262}$ inhibited ristocetin-dependent binding of [$^{125}$I]-vWF to platelets (Katagiri, Y., et al., *Thromb. Haemost.* 63:122–126 (1990)). In each case, the concentrations of synthetic peptide needed to inhibit vWF binding were substantially higher than the concentration of rGpIbaQ$_{221}$-L$_{318}$ effective in this example. While the I.C.$_{50}$ in this example ranged from 2 to $5 \times 10^{-7}$ M rGpIba polypeptide, the I.C.$_{50}$ for the most active synthetic peptides were 5 to $8 \times 10^{-4}$, 1,000 fold higher concentration (Vicente, V., et al., *J. Biol. Chem.* 265:274–280 (1990); Katagiri, Y., et al., *Thromb. Haemost.* 63:122–126 (1990)).

This strongly suggests that the synthetic peptides tested spanned only a portion of the vWF binding sequence or were not in an optimal conformation. Since reduction and alkylation of the recombinant GpIba polypeptide abolished all biologic activity over the concentration range tested (up to 3 μM polypeptide), cysteine residues 248 and 264 must form a disulfide bond in the native molecule that is essential for proper folding and optimizes biologic activity. None of the peptides tested in previous studies included both these cysteines and, thus, could not form this critical disulfide bond.

Although the primary vWF binding region of GpIba has now been clearly defined, the physiologic event which promotes vWF binding to platelet GpIb/IX has not yet been clearly identified. The binding of soluble vWF multimers to platelet GpIb/IX can also be induced, in vitro, by a cationic cofactor like ristocetin or botrocetin or by enzymatic removal of terminal sialic acid residues from vWF (Koutts, T., et al., *Prog. Haematol.* II:113–145 (1979); Fujimura, Y., et al., *Blood* 70:985–988 (1987). This example clearly demonstrates that rGpIbα$Q_{221}$-$L_{318}$, like the synthetic peptides that have been previously studied, can bind to potential GpIb/IX binding sites on vWF multimers in the absence of any added cofactor or conformational change. This suggests that regulated binding to multimeric vWF may require additional GpIb/IX sequences not present in the recombinant polypeptide.

The concomitant inhibition of vWF binding to collagen observed in addition to the inhibition of the vWF-GpIb interaction by rGpIbalphaQ221-L318 was an unexpected finding. This example is the first attempt of which the inventors are aware, to analyze simultaneous interactions between GpIb, vWF and collagen using a soluble, high affinity receptor fragment as a ligand. Inhibition may result from the close proximity of the GpIb binding and collagen binding sites of vWF. Using tryptic fragments of purified vWF and synthetic peptides, Mohri et al. have localized the GpIb interaction site to two discontinuous sequences—amino acids 474–488 and 694–708 in the Al repeat of vWF (Mohri, H., et al., *J. Biol. Chem.* 263:17901–17904 (1988); Mohri, H., et al., *J. Biol. Chem.* 264:17361–17367 (1989)). One of two potential collagen binding sites lies in the same repeated sequence between residues 512 and 673 (Pareti, F. I., et al., *J. Biol. Chem.* 262:13835–13841 (1987)). Since the GpIb and collagen binding domains clearly overlap within the linear sequence of vWF, it may not be unreasonable for occupancy of one site to perturb vWF interaction via the second binding site. A more definitive analysis will require more information about the three-dimensional structure of the binding domain.

The mechanism for this inhibition is less certain. One possibility could be that binding of the recombinant GpIbα polypeptide to the GpIb binding domain of vWF prevents vWF binding to collagen by steric hindrance. However, monoclonal antibodies have been identified which can selectively block either the GpIb or collagen binding sites on vWF (Pareti, F. I., et al., *J. Biol. Chem.* 262:13835–13841 (1987)). Since monoclonal antibodies (MW 160,000) are approximately 12 times the size of the recombinant GpIbα polypeptide (MW 13,670), steric hindrance seems unlikely. A second more likely possibility is that occupancy of the GpIb binding site on vWF alters the conformation of its adjacent collagen binding domain so that it no longer interacts with collagen. Clearly, the inhibitory effect must be due to the interaction of rGpIbα with GpIb/IX binding sites on vWF multimers, as the rGpIbα polypeptide does not bind to collagen. There are some important differences between platelet bound GpIbα and the soluble receptor fragment derived from GpIbα that might explain the inhibition of vWF binding to collagen. For example, the leucine-rich repeats and the serine-threonine rich region to which 0-linked oligosaccharides attach, which bracket the primary vWF interaction site, are not expressed in the recombinant polypeptide (Lopez, J. A., et al., *Proc. Natl. Acad. Sci. U.S.A.* 84:5615–5619 (1987); Petersen, E., et al., *J. Biol. Chem.* (submitted)). Either of these regions of the GpIbα polypeptide, as well as the extracytoplasmic domains of GpI or GpIX, could modulate the GpIb-vWF interaction and account for the different properties of platelet bound GpIb/IX. For example, it has been previously shown that removal of 0-linked oligosaccharide from glycocalicin, a soluble proteolytic fragment of the GpIbα chain which contains the leucine rich repeats, and oligosaccharide rich region of GpIbα, impaired its ability to interact with vWF (Sixma, J. J., et al., *J. Clin. Invest.* 74:736–744 (1984)).

The production of a properly folded recombinant GpIbα polypeptide which binds to GpIb/IX binding sites on vWF with high affinity. Expression in *E. coli,* when combined with site specific mutagenesis, provides a convenient way to produce recombinant GpIbα polypeptides. It is of considerable interest that the recombinant GpIbα polypeptide disclosed here prevents vWF interactions with two important substrates—platelet surface GpIb/IX and immobilized collagent fibrils. The biologic properties of this soluble receptor fragment make it a critical element around which agents that can selectively inhibit shear-dependent platelet adhesion to vascular subendothelium may be produced. Such compounds have potential as antithrombotic drugs.

From the foregoing, those of skill will appreciate that, although specific embodiments of the invention have been described herein for illustrative purposes, various modifications may be made without deviating from the spirit and scope of the invention. Accordingly, the invention is not limited except as by the appended claims.

---

We claim:

1. A human platelet glycoprotein Ib receptor fragment, wherein said fragment has the ability to modulate platelet adhesion and said fragment of human platelet glycoprotein Ib receptor consists of amino acids 221-318 of human GpIbα.

2. The human platelet glycoprotein Ib receptor fragment of claim 1, wherein said fragment is capable of blocking the binding of vWF to collagen.

3. The human platelet glycoprotein receptor fragment of claim 1, wherein said fragment is produced by a cell selected from the group consisting of E. coli, COS, CHO and COS-7.

4. The human platelet glycoprotein receptor fragment of claim 1, wherein said fragment is produced in E. coli.

5. The human platelet glycoprotein Ib receptor fragment of claim 1, wherein said fragment is recombinantly produced.

6. A method of purifying von Willebrands Factor comprising contacting a sample containing von Willebrands Factor with a fragment of human platelet glycoprotein Ib receptor so as to form a complex between human vWF in said sample and said fragment, and removing said vWF from said fragment so as to obtain purified human vWF, wherein said fragment of human platelet glycoprotein Ib receptor consists of residues 221-318 of human GpIbα.

7. A method of detecting human vWF in a sample comprising contacting said sample with a human platelet glycoprotein Ib receptor fragment, wherein said fragment is detectably labeled and said fragment of human platelet glycoprotein receptor consists of amino acids 221-318 of human GpIbα, so as to form a complex between human vWF in said sample and said detectably labeled fragment, and detecting whether said detectably labeled fragment is bound to said vWF.

8. A kit for the detection of human vWF in a sample, comprising a container means comprising one or more containers, wherein one of said containers comprises a human glycoprotein Ib receptor fragment, wherein said fragment is detectably labeled and said fragment of human platelet glycoprotein Ib receptor consists of amino acid residues 221-318 of human GpIbα.

9. A pharmaceutical preparation comprising a human platelet glycoprotein Ib receptor fragment, wherein said fragment of human platelet glycoprotein receptor consists of amino acids 221-318 of human GpIbα.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
ATG  CGC  GCC  CGG  GGA  TCC  TCT  AGA  GTC  GAC  CTG  CAG  GAC  AAT  GCT  GAA  AAT    51
Arg  Ala  Arg  Gly  Ser  Ser  Arg  Val  Asp  Leu  Gln  Asp  Asn  Ala  Glu  Asn
 1             5                        10                       15
```

(2) INFORMATION FOR SEQ ID NO:2:

(i) SEQUENCE CHARACTERISTICS:
        (A) LENGTH: 72 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:2:

```
TCA TGG TCC ACT GCT TCT CTA GAG CTT ATC ATC GAT GAT AAG CTG TCA        48
Ser Trp Ser Thr Ala Ser Leu Gln Leu Ile Ile Asp Asp Lys Leu Ser
 1               5                  10                  15

AAC ATG AGA ATT AAA TCA ATC TAA                                        72
Asn Met Arg Ile Lys Ser Ile
                20
```